(12) United States Patent
Yamamoto et al.

(10) Patent No.: US 10,688,024 B2
(45) Date of Patent: Jun. 23, 2020

(54) CLEANING COMPOSITION

(71) Applicant: SHIN-ETSU CHEMICAL CO., LTD., Tokyo (JP)

(72) Inventors: Atsushi Yamamoto, Joetsu (JP); Shingo Niinobe, Joetsu (JP); Akira Kitamura, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/149,562

(22) Filed: Oct. 2, 2018

(65) Prior Publication Data
US 2019/0105241 A1  Apr. 11, 2019

(30) Foreign Application Priority Data

Oct. 11, 2017 (JP) .................. 2017-197583

(51) Int. Cl.
| | |
|---|---|
| C11D 1/02 | (2006.01) |
| C11D 3/22 | (2006.01) |
| A61K 8/04 | (2006.01) |
| A61K 8/44 | (2006.01) |
| A61K 8/46 | (2006.01) |
| A61K 8/73 | (2006.01) |
| A61Q 19/10 | (2006.01) |
| A61Q 5/02 | (2006.01) |
| A61K 8/36 | (2006.01) |
| C11D 3/00 | (2006.01) |

(52) U.S. Cl.
CPC ............ *A61K 8/046* (2013.01); *A61K 8/361* (2013.01); *A61K 8/44* (2013.01); *A61K 8/442* (2013.01); *A61K 8/463* (2013.01); *A61K 8/731* (2013.01); *A61Q 5/02* (2013.01); *A61Q 19/10* (2013.01); *C11D 3/0094* (2013.01); *C11D 3/225* (2013.01); A61K 2800/594 (2013.01); A61K 2800/5922 (2013.01)

(58) Field of Classification Search
CPC .. C11D 1/02; C11D 3/22; C11D 3/225; A61K 8/731
See application file for complete search history.

(56) References Cited

U.S. PATENT DOCUMENTS

2004/0053807 A1* 3/2004 Thomas ............... A61K 8/0208
                                                          510/438
2016/0375374 A1* 12/2016 Ko ......................... A63H 33/28
                                                          106/162.8

FOREIGN PATENT DOCUMENTS

| JP | 2010-270085 A | 12/2010 |
|---|---|---|
| JP | 2014-218465 A | 11/2014 |
| WO | 91/13138 A1 | 9/1991 |
| WO | 2009/061779 A1 | 5/2009 |

OTHER PUBLICATIONS

Feb. 11, 2019 Extended Search Report issued in European Patent Application No. 18199322.1.

* cited by examiner

Primary Examiner — Brian P Mruk
(74) Attorney, Agent, or Firm — Oliff PLC

(57) ABSTRACT

A cleaning composition having good foamability and being capable of producing fine and stable foams with resilient texture, more specifically, a cleaning composition including a surfactant, methyl cellulose, hydroxypropyl methyl cellulose, and a solvent.

8 Claims, No Drawings

CLEANING COMPOSITION

BACKGROUND OF THE INVENTION

1. Field of the Invention

The invention relates to a cleaning composition.

2. Related Art

Regarding cleaning, cleaning compositions comprising various types of surfactants and cellulose derivatives have been conventionally developed for the purpose of improving foamability, foam texture (foam firmness), foam fineness, and foam stability.

Examples of such cleaning compositions may include a cleaning composition described in JP 2014-218465A, which is aimed at improving the speed of lathering (foamability), foam fineness and foam stability, and which comprises (A) at least one surfactant selected from amino acid surfactants and fatty acid soaps, and (B) a modified alkyl hydroxyalkyl cellulose which has been modified with at least one alkyl group having 2 or 3 carbon atoms and at least one hydroxyalkyl group having 2 or 3 carbon atoms, and optionally further modified with a methyl group.

SUMMARY OF THE INVENTION

However, the cleaning composition as described in JP-A 2014-218465A, which is merely a combination of the surfactant and the modified cellulose, is still unsatisfactory in foamability, foam fineness and foam stability. Accordingly, an object of the invention is to provide a cleaning composition having good foamability and being capable of producing fine and stable foams with resilient texture.

As a result of extensive research to achieve the object, the inventors have found that a cleaning composition having good foamability and being capable of producing fine and stable foams with resilient texture can be obtained by using both of methyl cellulose and hydroxypropyl methyl cellulose, and have completed the invention.

In one aspect of the invention, there is provided a cleaning composition comprising a surfactant, methyl cellulose, hydroxypropyl methyl cellulose, and a solvent.

According to the invention, the cleaning composition having good foamability and being capable of producing fine and stable foams with resilient texture can be obtained.

DETAILED DESCRIPTION OF THE PREFERRED EMBODIMENTS

Hereinafter, the cleaning composition comprising a surfactant, methyl cellulose, hydroxypropyl methyl cellulose and a solvent will be described in detail.

(1) Surfactant

Examples of the surfactant include an anionic surfactant, a cationic surfactant, an ampholytic surfactant, and a nonionic surfactant.

Examples of the anionic surfactant include a fatty acid salt, an amino acid salt, an alkyl sulfate ester salt, an alkyl ether sulfate salt, a phosphate ester salt, a sulfonate salt, and a sulfosuccinate ester salt.

Examples of the fatty acid salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of fatty acid having preferably 6 to 24 carbon atoms, more preferably 12 to 20 carbon atoms. Examples of the fatty acid include capric acid (C10), lauric acid (C12), myristic acid (C14), palmitic acid (C16), stearic acid (C18), isostearic acid (C18), arachidic acid (C20), behenic acid (C22), oleic acid (C18), linoleic acid (C18), linolenic acid (C18), and arachidonic acid (C20).

Examples of the fatty acid salt preferably include sodium laurate (C12), potassium laurate (C12), potassium myristate (C14), and triethanolamine laurate (C18).

Examples of the amino acid salt include a glutamic acid salt, a glycine salt, an alanine salt, a sarcosine salt, and an aspartic acid salt.

Examples of the glutamic acid salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of a glutamic acid such as cocoyl glutamic acid, N-cocoyl-L-glutamic acid, N-lauroyl-L-glutamic acid, N-myristoyl-L-glutamic acid, N-stearoyl-L-glutamic acid, and N-acyl-L-glutamic acid.

Examples of the glycine salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of a glycine such as N-cocoylglycine, lauroylglycine, myristoylglycine, and stearoylglycine.

Examples of the alanine salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of an alanine such as N-cocoyl-DL-alanine, lauroylalanine, myristoylalanine, stearoylalanine, hydroxyethylhydroxyalkyl-β-alanine, cocoyl methyl alanine, lauroylmethyl-β-alanine, N-lauroyl-N-methyl-β-alanine, and myristoylmethyl-β-alanine.

Examples of the sarcosine salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of a sarcosine such as cocoyl sarcosine, N-cocoyl sarcosine, lauroyl sarcosine, myristoyl sarcosine, and stearoyl sarcosine.

Examples of the aspartic acid salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of an aspartic acid such as N-cocoyl-L-aspartic acid, N-lauroyl-L-aspartic acid, N-myristoyl-L-aspartic acid, N-stearoyl-L-aspartic acid, and N-acyl-L-aspartic acid.

Examples of the amino acid salt preferably include sodium cocoyl glutamate, sodium N-lauroyl-L-aspartate, sodium cocoyl sarcosinate, and triethanolamine cocoyl sarcosinate.

Examples of the alkyl sulfate ester salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of an alkyl sulfate monoester having preferably 12 to 20 carbon atoms, more preferably one having 12 to 15 carbon atoms, such as lauryl sulfate (C12), or stearyl sulfate (C18).

Examples of the alkyl sulfate ester salt preferably include sodium lauryl sulfate and sodium stearyl sulfate.

Examples of the alkyl ether sulfate salt include a polyoxyethylene alkyl ether sulfate salt such as sodium laureth sulfate.

Examples of the phosphate ester salt include an alkali metal salt (e.g. a sodium or potassium salt), an ammonium salt, or an amine salt (e.g. a salt of a primary, secondary or tertiary amine having 1 to 6 carbon atoms, such as a salt of triethanolamine) of an alkyl phosphate monoester having preferably 12 to 26 carbon atoms, more preferably 12 to 15 carbon atoms, such as lauryl phosphate.

Examples of the phosphate ester salt preferably include sodium lauryl phosphate.

Examples of the sulfonate salt include sodium dodecyl benzene sulfonate.

Examples of the sulfosuccinate ester salt include disodium laureth sulfosuccinate.

The other examples of the anionic surfactant include sodium methyl cocoyl tauate, sodium methyl lauroyl tauate, sodium methyl cocoyl tauate, DL-pyrrolidonecarboxylic acid salt of N-cocoyl-L-arginine ethyl ester, N-acyl taurates, N-acyl methyl taurates, sodium N-lauroyl-N'-carboxymethyl-N'-hydroxyethyl ethylene diamine, 2-alkyl-N'-carboxymethyl-N'-hydroxyethyl imidazolinium betaine, sodium polyoxyethylene lauryl ether phosphate, sodium polyoxyethylene lauryl ether acetate, sodium polyoxyethylene alkyl sulfosuccinate, sodium polyoxyethylene coconut fatty acid monoethanolamide sulfate.

Examples of the cationic surfactant include an alkyl-type quaternary ammonium salt and a benzalkonium-type quaternary ammonium salt.

Examples of the alkyl-type quaternary ammonium salt include stearyl trimethyl ammonium chloride, and behentrimonium chloride.

Examples of the benzalkonium-type quaternary ammonium salt include benzalkonium chloride, and benzethonium chloride.

Examples of the ampholytic surfactant include a betaine-type ampholytic surfactant and an amino acid-type ampholytic surfactant.

Examples of the betaine-type ampholytic surfactant include an alkyl betaine such as lauryl dimethylaminoacetic acid betaine and stearyl dimethylaminoacetic acid betaine; imidazoline-type betaine such as sodium cocoamphoacetate; and alkylamide propyl betaine such as lauramidopropyl betaine and cocamidopropyl betaine.

Examples of the amino acid-type ampholytic surfactant include sodium β-laurylaminopropionate.

Examples of the nonionic surfactant include a sorbitan fatty acid ester, a glycerine fatty acid ester, and a polysorbate.

Examples of the sorbitan fatty acid ester include sorbitan laurate, and sorbitan palmitate.

Examples of the glycerine fatty acid ester include glyceryl stearate.

Examples of the polysorbate include polysorbate 20, polysorbate 60, and polysorbate 80.

The surfactant may be used alone or in combination of two or more. However, if two or more surfactants having opposite charges, i.e. one having positive charge and another having negative charge, are mixed, agglomeration may occur due to static attraction between different charges, leading to decreased compatibility. Hence, an anionic or cationic surfactant is, when used in combination with another surfactant, preferably combined with a nonionic and/or ampholytic surfactant.

The surfactant is preferably an anionic surfactant from the standpoint of the washability or foamability.

The content of the surfactant in the cleaning composition may be preferably from 1 to 40% by mass, more preferably from 10 to 25% by mass, from the standpoint of the compatibility of the surfactant with the methyl cellulose and the hydroxypropyl methyl cellulose in the composition.

(2) Methyl Cellulose and Hydroxypropyl Methyl Cellulose
(2-1) Methyl Cellulose

A viscosity at 20° C. of a 2.0% by mass aqueous solution of the methyl cellulose is preferably from 1.0 to 100.0 mPa·s, more preferably from 2.0 to 50.0 mPa·s, still more preferably from 3.0 to 10.0 mPa·s. When the viscosity is less than 1.0 mPa·s, the surface activity of the cleaning composition may become unsatisfactory so that sufficient foamability or foam stability may not be obtained. When the viscosity is more than 100.0 mPa·s, the cleaning composition may become too viscous so that it may become difficult to lather or to make foams, or it may cause clogging of a filter in a foam container. The viscosity at 20° C. of the 2.0% by mass aqueous solution may be determined with an Ubbelohde-type viscometer in accordance with the Viscosity Measurement by Capillary Tube Viscometer described in General Tests in the Japanese Pharmacopoeia 17th Edition.

The methyl cellulose has a degree of substitution (DS) of the methoxy groups of preferably from 1.00 to 2.20, more preferably from 1.50 to 2.00, still more preferably from 1.70 to 1.90, from the standpoint of the compatibility with the solvent. The degree of substitution (DS) is an average number of methoxy-substituted hydroxyl groups per glucose ring of the cellulose. The DS can be calculated from the values obtained by the assay method of methyl cellulose described in the Japanese Pharmacopoeia 17th Edition.

A 1.5% by mass aqueous solution of the methyl cellulose has a storage modulus at 65° C., which may be expressed as G'(65° C.), of preferably from 100 to 2,500 Pa, more preferably from 1,000 to 2,500 Pa, still more preferably from 2,000 to 2,500 Pa, from the standpoint of improved foam retention time and foam fineness.

In general, the storage modulus G' represents an elastic factor of a solution, i.e. a factor characterized by the ability to return from deformation caused by a force to the original form after removal of the force. The storage modulus is an index of gel strength. In other words, the gel strength of methyl cellulose may be represented by a storage modulus at 65° C.: G'(65° C.) of a 1.5% by mass aqueous solution thereof. The storage modulus at 65° C.: G'(65° C.) of a 1.5% by mass aqueous solution of methyl cellulose may be determined with a rheometer such as MCR 502 from Anton Paar Co.

The 1.5% by mass aqueous solution of methyl cellulose is prepared by a method comprising steps of: placing an exact amount of methyl cellulose equivalent to 4.50 g on the dried basis in a wide-mouth bottle (container having a diameter of 65 mm, a height of 120 mm and a volume of 350 ml); adding hot water of 98° C. thereto to obtain 300.0 g as a mixture; sealing the container with a stopper; stirring the mixture with a stirrer at 350 to 450 rpm for 20 minutes to get a homogeneous dispersion; and dissolving the methyl cellulose in water of the dispersion with stirring in a water bath of 0 to 5° C. for 40 minutes to obtain a solution, which will be used as a sample solution.

The storage modulus G'(65° C.) of methyl cellulose may be determined by the method comprising steps of: adding the 1.5% by mass aqueous solution of methyl cellulose as prepared above into a CC27 measurement cup (a cylindrical aluminum container having a diameter of 30 mm and a height of 80 mm) up to a marked line (25 ml), while keeping a sample measurement section of the rheometer at a temperature of 65° C.; applying oscillatory stress at an angular frequency of 1 rad/s and an amplitude of 10% by means of a bob cylinder (a diameter of 26.7 mm and a height of 40.0 mm: CC27) to start the measurement in the sample measurement section; and collecting the data at a point every minute, while keeping the temperature of the measurement section constant at 65° C. The storage modulus G'(65° C.) refers to the maximum value of storage modulus measured in the period of from the start of the measurement to 60 minutes thereafter.

Methyl cellulose may be one specifically prepared for use in the cleaning composition, or may be one which is commercially available. It is preferable to use methyl cellulose which has been specifically prepared for use in the cleaning composition from the standpoint of controllability of the storage modulus G'(65° C.) of a 1.5% by mass aqueous solution of the methyl cellulose.

Methyl cellulose may be produced by the method comprising steps of: bringing cellulose pulp, such as wood pulp or linter pulp, into contact with an alkali metal hydroxide solution, such as a 10 to 60% by mass aqueous solution of sodium hydroxide or potassium hydroxide, to obtain alkali cellulose; and reacting the alkali cellulose with a methylating agent. The methyl cellulose thus obtained may be optionally depolymerized with an acid to produce methyl cellulose capable of providing the desired viscosity.

Methyl cellulose having a storage modulus at 65° C.: G'(65° C.) of from 100 to 2,500 Pa, as measured in a 1.5% by mass aqueous solution, may be produced by the method comprising steps of: two or more addition steps of adding an alkali metal hydroxide solution, such as a 10 to 60% by mass aqueous solution of sodium hydroxide or potassium hydroxide; and reacting with a methylating agent. For example, the methyl cellulose may be produced by a method comprising steps of: bringing cellulose pulp into contact with a first alkali metal hydroxide solution to obtain alkali cellulose; reacting the alkali cellulose with an methylating agent to obtain a first reaction product mixture; adding a second alkali metal hydroxide solution to the first reaction product mixture with stirring, without addition of the methylating agent, to obtain a second reaction product mixture; and purifying the second reaction product mixture to obtain the methyl cellulose, wherein a mass ratio of a first alkali metal hydroxide in the first alkali metal hydroxide solution to a total weight of the first alkali metal hydroxide and a second alkali metal hydroxide in the second alkali metal hydroxide solution is preferably from 50 to 86%.

The cellulose pulp is preferably in the form of a sheet or chips from the standpoint of easy handling and draining of the alkali cellulose.

The pulp sheet preferably has an alpha-cellulose content of 90% by mass or more from the standpoint of suppressing a decrease in the alkali absorption rate and reducing the number of undissolved fibers. The alpha-cellulose content may be determined in accordance with TEST METHOD T429 by TAPPI (Technical Association of the Pulp and Paper Industry).

Regarding an amount of the first alkali metal hydroxide solution to be used, a molar ratio of the first alkali metal hydroxide to the cellulose in the cellulose pulp (i.e. first alkali metal hydroxide/cellulose) is preferably from 2.00 to 4.00, more preferably from 2.70 to 3.50.

It should be noted that the molar amount of cellulose in the cellulose pulp refers to a value obtained by dividing the mass of the solid component by 162, i.e. the molecular weight of $C_6H_{10}O_5$ which is the structural unit of cellulose, because the solid component is presumed to correspond to the cellulose in the cellulose pulp. The solid component in the cellulose pulp is a component other than water in the cellulose pulp. The solid component in the cellulose pulp typically contains alpha-cellulose as a main component; organic matters such as hemicellulose, lignin and resins; and inorganic matters such as Si and Fe. An amount of the solid component in the cellulose pulp may be calculated from the dry matter content determined by the method specified in JIS P8203:1998 Determination of Dry Matter Content for Pulp. The dry matter content is a ratio of the mass of a sample after dried at 105±2° C. until reaching constant mass to the mass of a sample before dried, and is expressed in mass % or percent by mass.

The inside temperature of the reactor when the cellulose pulp is brought into contact with the first alkali metal hydroxide, preferably the inside temperature of the reactor when the first alkali metal hydroxide solution is added to the cellulose pulp, is preferably from 10 to 80° C., more preferably from 30 to 70° C., from the standpoint of formation of uniform alkali cellulose.

The addition rate of the first alkali metal hydroxide in the first alkali metal hydroxide solution means a molar amount of the first alkali metal hydroxide added per unit time and per mol of cellulose in the cellulose pulp, and is preferably from 1.50 to 48.00 [mol/mol·hr], more preferably from 4.80 to 18.60 [mol/mol·hr], still more preferably from 8.00 to 15.00 [mol/mol·hr], from the standpoint of uniform mixing of the first alkali metal hydroxide solution in the system.

It is also possible to continue the mixing with stirring, after the addition of the first alkali metal hydroxide solution is completed, for further 5 to 30 minutes to make the alkali cellulose more uniform.

It is also possible to add an organic solvent which does not affect the methylation, such as dimethyl ether, to the system before, during or after the addition of the first alkali metal hydroxide solution, in order to suppress local heat generation in the reactor.

Then, the alkali cellulose thus obtained is reacted with a methylating agent to obtain a first reaction product mixture. Examples of the methylating agent include methyl chloride.

The inside temperature of the reactor during the reaction with the methylating agent is preferably from 40 to 90° C., more preferably from 50 to 80° C., from the standpoint of the reaction control.

Regarding an amount of the methylating agent, a molar ratio of the methylating agent to the total of the first and second alkali metal hydroxides (methylating agent/total of alkali metal hydroxides) is preferably from 0.8 to 1.5, more preferably from 1.0 to 1.3.

The methylating agent is preferably added to the alkali cellulose.

The methylating agent is added over a period of preferably from 30 to 120 minutes, more preferably 40 to 90 minutes, from the standpoint of the reaction control and productivity.

The first reaction product mixture thus obtained may be optionally purified by the same purification method as the conventional method for purifying crude methyl cellulose to obtain methyl cellulose. Examples of the purification method include washing crude methyl cellulose with hot water of 90° C. or higher.

The methyl cellulose in the first reaction product mixture has a degree of substitution (DS) of methoxy groups of preferably from 0.75 to 1.68, more preferably from 0.81 to 1.68, still more preferably from 0.99 to 1.37, from the standpoint of obtaining the desired viscosity or storage modulus.

Then, the methylated first reaction product mixture is subjected to addition of a second alkali metal hydroxide solution with stirring, in the absence of further addition of the methylating agent, to obtain a second reaction product mixture.

The timing of the addition of the second alkali metal hydroxide solution to the first reaction product mixture, in other words, the start time of the addition of the second alkali metal hydroxide solution, is preferably after the addition of at least 80% by mass of the total amount of the methylating agent is completed, more preferably after the addition of all of the total amount of the methylating agent is completed.

Regarding an amount of the second alkali metal hydroxide solution, a molar ratio of the second alkali metal hydroxide to the cellulose in the starting cellulose pulp (i.e. second alkali metal hydroxide/cellulose) is preferably from 0.65 to 2.00, more preferably from 0.88 to 1.48, and a ratio of the mass of the first alkali metal hydroxide in the first alkali metal hydroxide solution to the total mass of the first and second alkali metal hydroxides in the first and second alkali metal hydroxide solutions is preferably 50 to 86%, more preferably 65 to 80%, still more preferably 65 to 75%.

The inside temperature of the reactor at the start of blending the first reaction product mixture with the second alkali metal hydroxide solution, preferably the inside temperature of the reactor at the start of the addition of the second alkali metal hydroxide solution to the first reaction product mixture, is preferably from 65 to 90° C., more preferably from 75 to 85° C.

The addition rate of the second alkali metal hydroxide in the second alkali metal hydroxide solution means a molar amount of the second alkali metal hydroxide added to the first reaction product mixture per unit time and per mol of cellulose in the starting cellulose pulp, and is preferably from 0.5 to 9.6 [mol/mol·hr], more preferably from 1.0 to 6.5 [mol/mol·hr], still more preferably from 1.0 to 3.5 [mol/mol·hr].

The inside temperature of the reactor during the mixing with stirring after the addition of the second alkali metal hydroxide solution is completed, is preferably from 80 to 120° C., more preferably from 85 to 100° C. from the standpoint of the reaction control. It is possible to apply heat after the addition of the second alkali metal hydroxide solution is completed, so as to allow the reaction to be completed.

The time for the mixing with stirring after the addition of the second alkali metal hydroxide solution is completed, is preferably 10 to 60 minutes, more preferably 20 to 40 minutes from the standpoint of productivity.

The second reaction product mixture thus obtained may be purified in the same purification method as the conventional method for purifying crude methyl cellulose. Examples of the purification method preferably include washing crude methyl cellulose with hot water of 90° C. or higher.

The methyl cellulose thus obtained may be optionally depolymerized with an acid to obtain methyl cellulose having a desired viscosity.

(2-2) Hydroxypropyl Methyl Cellulose

A 2.0% by mass aqueous solution of the hydroxypropyl methyl cellulose has a viscosity at 20° C. of preferably from 1.0 to 100.0 mPa·s, more preferably from 2.0 to 50.0 mPa·s, still more preferably from 3.0 to 10.0 mPa·s. When the viscosity is less than 1.0 mPa·s, the surface activity of the cleaning composition may become unsatisfactory so that sufficient foamability or foam stability may not be obtained. When the viscosity is more than 100.0 mPa·s, the cleaning composition may become too viscous so that it may become difficult to lather or to make foams, or it may cause clogging of a filter in a foam container. The viscosity at 20° C. of a 2% by mass aqueous solution may be determined with an Ubbelohde-type viscometer in accordance with the Viscosity Measurement by Capillary Tube Viscometer described in General Tests in the Japanese Pharmacopoeia 17th Edition.

The hydroxypropyl methyl cellulose has a degree of substitution (DS) of the methoxy groups of preferably from 1.00 to 2.20, more preferably from 1.40 to 2.00, from the standpoint of the compatibility with the solvent. The degree of substitution (DS) is an average number of methoxy-substituted hydroxyl groups per glucose ring of the cellulose.

The hydroxypropyl methyl cellulose has a molar substitution (MS) of the hydroxypropoxy groups of preferably from 0.10 to 0.60, more preferably from 0.15 to 0.35, from the standpoint of the compatibility with the solvent. The molar substitution (MS) is an average number of hydroxypropoxy groups incorporated per glucose ring of the cellulose. The DS and MS may be calculated from the values obtained by the assay method of hydroxypropyl methyl cellulose, as described in the Japanese Pharmacopoeia 17th Edition.

The hydroxypropyl methyl cellulose has a storage modulus at 65° C.: G'(65° C.) of preferably from 0.10 to 10.00 Pa, as measured in a 1.5% by mass aqueous solution thereof, from the standpoint of stable surface activity.

The storage modulus G'(65° C.) of a 1.5% by mass aqueous solution of the hydroxypropyl methyl cellulose may be determined in the same manner as that of the methyl cellulose.

The hydroxypropyl methyl cellulose may be one specifically produced for use in the cleaning composition, or may be one which is commercially available.

The hydroxypropyl methyl cellulose may be produced by the method comprising steps of: bringing cellulose pulp, such as wood pulp or linter pulp, into contact with an alkali metal hydroxide solution, such as a 10 to 60% by mass aqueous solution of sodium hydroxide or potassium hydroxide, to obtain alkali cellulose; and reacting the alkali cellulose with a methylating agent and a hydroxypropylating agent. The hydroxypropyl methyl cellulose thus obtained may be optionally depolymerized with acid to obtain hydroxypropyl methyl cellulose having a desired viscosity.

The mass ratio of the methyl cellulose to the hydroxypropyl methyl cellulose is in a range of preferably from 40:60 to 80:20, more preferably from 50:50 to 70:30, still more preferably from 55:45 and 65:40. When the methyl cellulose portion is less than 40/100, it may become difficult to obtain fine foam having stability or resilient feeling. When the hydroxypropyl methyl cellulose portion is less than 20/100, it may become difficult to obtain fine foam.

The total content of the methyl cellulose and the hydroxypropyl methyl cellulose in the cleaning composition is from 0.1 to 10.0% by mass, more preferably from 0.5 to 5.0% by mass, still more preferably from 1.0 to 3.0% by mass, from the standpoint of improvement of the foamability and foam stability.

(3) Solvent

Examples of the solvent include water and a mixed solvent of water and at least one hydrophilic solvent.

Purified water is preferable as water from the standpoint of the reduced amount of impurities.

Examples of the hydrophilic solvent include a polyol and a lower alcohol having 1 to 3 carbon atoms. Examples of the polyol include polyhydric alcohols having 2 to 6 carbon atoms, such as propylene glycol, dipropylene glycol, hexylene glycol, 1,3-butylene glycol, glycerine and sorbitol. Examples of the lower alcohol having 1 to 3 carbon atoms include methanol, ethanol and isopropyl alcohol. The hydrophilic solvent may be used alone or in combination of two or more.

The mass ratio of the water to the hydrophilic solvent in the mixed solvent is preferably from 90:10 to 10:90, from the standpoint of the compatibility with the surfactant, the methyl cellulose and the hydroxypropyl methyl cellulose.

The content of the solvent in the cleaning composition is from 50.0 to 98.9% by mass, more preferably from 60.0 to 90.0% by mass, from the standpoint of the compatibility with the surfactant, the methyl cellulose and the hydroxypropyl methyl cellulose.

(4) Additive

The cleaning composition may further comprise one or more optional additives such as a viscosity modifier, an adjuvant, a chelating agent, an antifoaming agent, a fragrance and a coloring agent.

Examples of the viscosity modifier include a natural polymer such as carrageenan, pectin, starch and xanthan gum; a semisynthetic polymer such as carboxymethyl cellulose and cationized cellulose; and a synthetic polymer such as polyvinyl alcohol and polyethylene glycol. The content of the viscosity modifier in the cleaning composition may be preferably from 0.1 to 10.0% by mass from the standpoint of the compatibility and adjustment into the preferable viscosity.

Examples of the adjuvant include an alkali metal salt of polyvalent carboxylic acid, such as sodium citrate and sodium malate; and an alkali adjuvant such as caustic soda, soda ash, ammonia, triethanolamine, sodium tripolyphosphate and sodium silicate. The content of the adjuvant in the cleaning composition may be preferably from 0.5 to 10.0% by mass from the standpoint of the compatibility.

Examples of the chelating agent include an amino polycarboxylic acid-type chelating agent such as EDTA and NTA. The content of the chelating agent in the cleaning composition may be preferably from 0.5 to 10.0% by mass from the standpoint of the compatibility.

Examples of the antifoaming agent include a silicone-type antifoaming agent such as KF-96 (dimethylpolysiloxane); and a sorbitan fatty acid ester-type antifoaming agents such as sorbitan trioleate. The content of the antifoaming agent in the cleaning composition may be preferably from 0.01 to 10.00% by mass, more preferably from 0.01 to 1.00% by mass, from the standpoint of the foam stability and rinsability.

Examples of the fragrance include a vegetable fragrance such as vanilla, mint and cinnamon; and an animal fragrance such as ambergris, castoreum and musk. The content of the fragrance in the cleaning composition may be preferably from 0.01 to 5.00% by mass from the standpoint of keeping an odor ingredient in the cleaning composition.

Examples of the coloring agent include kaolin, caramel, ultramarine, iron oxide, and talc. The content of the coloring agent in the cleaning composition may be preferably from 0.1 to 10.00% by mass, more preferably from 0.5 to 5.0% by mass, from the standpoint of the color stability of the cleaning composition.

(5) Cleaning Composition

The cleaning composition has a viscosity at 20° C. of preferably from 10 to 2,000 mPa·s, more preferably from 20 to 1,000 mPa·s, still more preferably from 30 to 100 mPa·s, particularly preferably from 35 to 60 mPa·s, from the standpoint of suppression of surfactant precipitation, foamability and foam stability. When the viscosity of the cleaning composition is less than 600 mPa·s, the viscosity of the cleaning composition may be determined with an Ubbelohde-type viscometer in accordance with the Viscosity Measurement by Capillary Tube Viscometer described in General Tests in the Japanese Pharmacopoeia 17th Edition. When the viscosity of the cleaning composition is from 600 mPa·s to less than 1,000 mPa·s, the viscosity of the cleaning composition may be determined with a Brookfield viscometer using the No. 2 rotor at 30 rpm and 20° C. When the viscosity of the cleaning composition is from 1,000 mPa·s to 2,000 mPa·s, the viscosity of the cleaning composition may be determined with a Brookfield viscometer using the No. 3 rotor at 30 rpm and 20° C.

The cleaning composition has a zeta potential of preferably from −100 to −30 mV, more preferably from −75 to −30 mV, still more preferably from −60 to −30 mV from the standpoint of the compatibility of the surfactant, the methyl cellulose, the hydroxypropyl methyl cellulose and the solvent in the cleaning composition. The zeta potential of the cleaning composition may be determined with a zeta potential analyzer such as ELSZ-2000 (Otsuka Electronics Co., Ltd. (Osaka, Japan)).

The cleaning composition may be produced by, for example, the method comprising steps of: mixing the surfactant, methyl cellulose, hydroxypropyl methyl cellulose, and hot water (70-100° C.) with stirring to obtain a predetermined mass of dispersion of methyl cellulose and hydroxypropyl methyl cellulose; and stirring the dispersion in a water bath of 0 to 5° C. to dissolve the methyl cellulose and the hydroxypropyl methyl cellulose in water of the dispersion.

Although depending on the type of the surfactant, it may be necessary to heat the mixture of the surfactant, methyl cellulose, hydroxypropyl methyl cellulose and water to a temperature of from 70 to 80° C. in order to dissolve the surfactant in the water. In this case, it is preferably to stir the mixture with a stirrer in a bath of 70 to 100° C. until a uniform dispersion is obtained.

The cleaning composition may be preferably a skin or hair cleaning composition which may be suitably used for, for example, a face wash, a hand soap, a body soap or a shampoo.

The cleaning composition may be placed in a foamer container which discharges its liquid content into the form of foam upon use. Any foamer container capable of mixing the cleaning composition with air for discharging them into the form of foam may be used without any further limitation. Examples of the foamer container include a squeeze foamer container which is capable of dispensing foam by hand-squeezing the bottle body portion, and a pump foamer container which is capable of dispensing foam by pushing down the nozzle portion. A suitable container may be selected depending on the intended use. Specific examples of the squeeze foamer container include those commercially available from Daiwa Can Company. Specific examples of the pump foamer container include AWAKOBO Handy available from The Buyer's, Inc.

As described above, the cleaning composition having good foamability and being capable of producing fine and stable foam with resilient texture can be produced.

EXAMPLES

The invention is further described with reference to the following Synthesis Examples, Examples and Comparative Examples. It should not be construed that the invention is limited to or by them.

Synthesis Example 1

<Production of Methyl Cellulose (MC-1)>

Wood pulp having an intrinsic viscosity of 1,350 mL/g was pulverized with a pulverizer to obtain cellulose pulp powder. The cellulose pulp powder in an amount corresponding to 6.0 kg of cellulose was placed in a pressure reactor equipped with a jacket and an internal stirrer. Vacuum and nitrogen purging were conducted to thoroughly remove oxygen from the reactor.

Then, the inside of the reactor was stirred, while maintaining the inside temperature of the reactor at 60° C. A 49% by mass aqueous solution of sodium hydroxide was added thereto at one stage at an addition rate of 18.88 [mol/mol·hr] in such an amount that a molar ratio of the sodium hydroxide in the aqueous sodium hydroxide solution to the cellulose in the starting cellulose pulp (sodium hydroxide/cellulose) was 4.72, to form alkali cellulose.

Subsequently, 2.4 kg of dimethyl ether was added thereto, while keeping the inside temperature of the reactor at 60° C. After the addition of dimethyl ether was completed, methyl chloride was added thereto over a period of 60 minutes in such an amount that a molar ratio of the methyl chloride to the sodium hydroxide (methyl chloride/sodium hydroxide) was 1.1, while increasing the inside temperature of the reactor from 60 to 80° C.

After the addition of the methyl chloride was completed, the etherification was conducted for 70 minutes, while increasing the inside temperature of the reactor from 80 to 95° C., to obtain crude methyl cellulose.

The crude methyl cellulose thus obtained was then purified and pulverized to obtain methyl cellulose. The obtained methyl cellulose (1.0 kg) was placed in a 20-L Henschel mixer, and was subjected to spray of a 12% by mass hydrochloric acid, while stirred at 200 rpm. The amount of hydrochloric acid sprayed was 0.3% by mass relative to the amount of the methyl cellulose. Fifty grams of the resulting mixture was transferred to a 500-mL glass reactor, and the reactor was rotated for 60 minutes while heated in a water bath of 80° C. to allow the reaction to proceed. The reactor was vacuumed at 80° C. to a pressure of 60 mmHg for 60 minutes to evaporate hydrogen chloride and water. Sodium bicarbonate in an amount corresponding to ½ mole of the added hydrochloric acid was added thereto for neutralization.

Regarding the resulting methyl cellulose (MC-1), a viscosity at 20° C. in a 2.0% by mass aqueous solution thereof, a degree of substitution (DS) of the methoxy groups, and a storage modulus at 65° C.: G'(65° C.) of a 1.5% by mass aqueous solution thereof are shown in Table 1.

Synthesis Example 2

<Production of Methyl Cellulose (MC-2)>

Cellulose pulp was placed in a reactor in the same manner as in Synthesis Example 1. Then, the inside of the reactor was stirred, while maintaining the inside temperature of the reactor at 60° C. A 49% by mass aqueous solution of sodium hydroxide, as the first alkali metal hydroxide solution, was added thereto at an addition rate of 10.48 [mol/mol·hr] in such an amount that a molar ratio of the first sodium hydroxide in the first sodium hydroxide solution to the cellulose in the starting cellulose pulp (first sodium hydroxide/cellulose) was 2.62, to form an alkali cellulose.

Subsequently, 2.4 kg of dimethyl ether was added thereto, while keeping the inside temperature of the reactor at 60° C. After the addition of dimethyl ether was completed, methyl chloride was added thereto over a period of 60 minutes in such an amount that a molar ratio of methyl chloride to the total of the first and later second sodium hydroxides (methyl chloride/total sodium hydroxide) was 1.1, while increasing the inside temperature of the reactor from 60° C. to 80° C., to obtain a first reaction product mixture. Subsequent to the addition of methyl chloride, a 49% by mass aqueous sodium hydroxide solution, as the second alkali metal hydroxide solution, was added thereto at an addition rate of 3.20 [mol/mol·hr] in such an amount that a molar ratio of the second sodium hydroxide in the second sodium hydroxide solution to the cellulose in the cellulose pulp (second sodium hydroxide/cellulose) was 1.60, to obtain a second reaction product mixture. The inside temperature of the reactor was 77° C. at the beginning of the addition of the second aqueous sodium hydroxide solution, and was increased at a rate of 24° C./hr during the addition of the second aqueous sodium hydroxide solution, i.e. from the beginning to the completion of the addition. After the completion of the addition of the second aqueous sodium hydroxide solution, the stirring was continued for further 30 minutes to complete the etherification. A ratio of the mass of the first sodium hydroxide in the first sodium hydroxide solution to the total mass of the first and second sodium hydroxides in the first and second aqueous sodium hydroxide solutions was 62.1%.

The second reaction product mixture thus obtained was made into a slurry by the addition of hot water of 95° C., then washed with a rotary pressure filter, and dried with an fan dryer. The dried product was pulverized with a ball mill and classified through a sieve to obtain methyl cellulose. Then, the depolymerization was carried out to adjust the viscosity in the same manner as in Synthesis Example 1.

Regarding the resulting methyl cellulose (MC-2), a viscosity at 20° C. in a 2.0% by mass aqueous solution thereof, a degree of substitution (DS) of the methoxy group, and a storage modulus at 65° C.: G'(65° C.) of a 1.5% by mass aqueous solution thereof, are shown in Table 1.

Synthesis Example 3

<Production of Hydroxypropyl Methyl Cellulose (HPMC-1)>

Cellulose pulp was placed in a reactor in the same manner as in Synthesis Example 1. Then, the inside of the reactor was stirred, while maintaining the inside temperature of the reactor at 60° C. A 49% by mass aqueous solution of sodium hydroxide was added at one stage at an addition rate of 18.88 [mol/mol·hr] in such an amount that a molar ratio of the sodium hydroxide in the aqueous sodium hydroxide solution to the cellulose in the starting cellulose pulp (sodium hydroxide/cellulose) was 4.72, to form an alkali cellulose.

Subsequently, 2.4 kg of dimethyl ether was added thereto, while keeping the inside temperature of the reactor at 60° C. After the addition of the dimethyl ether was completed, methyl chloride and propylene oxide were introduced thereto at the same time, while increasing the inside temperature of the reactor from 60 to 80° C., The methyl chloride was added over a period of 60 minutes in such an amount that a molar ratio of the methyl chloride to the sodium hydroxide (methyl chloride/sodium hydroxide) was 1.1. Propylene oxide was added over a period of 40 minutes in such an amount that a molar ratio of the propylene oxide to the cellulose in the starting cellulose pulp (propylene oxide/cellulose) was 1.5.

The etherification was conducted for 70 minutes, while increasing the temperature from 80 to 95° C., to obtain crude hydroxypropyl methyl cellulose.

The crude methyl cellulose thus obtained was then purified and pulverized to obtain hydroxypropyl methyl cellulose, as in Synthesis Example 1. Then, the depolymerization was carried out to adjust the viscosity in the same manner as in Synthesis Example 1.

Regarding the resulting hydroxypropyl methyl cellulose (HPMC-1), a viscosity at 20° C. of a 2.0% by mass aqueous solution thereof, a degree of substitution (DS) of the methoxy group, a molar substitution (MS) of the hydroxypropoxy group, and a storage modulus at 65° C.: G'(65° C.) of a 1.5% by mass aqueous solution thereof are as shown in Table 1.

TABLE 1

|  | Viscosity (mPa · s) | DS | MS | Storage modulus G'(65° C.) (Pa) |
|---|---|---|---|---|
| MC-1 | 4.0 | 1.77 | — | 113 |
| MC-2 | 6.0 | 1.86 | — | 2100 |
| HPMC-1 | 5.6 | 1.90 | 0.25 | 0.22 |

Example 1

<Production of Cleaning Composition>

In a wide-mouth bottle (container having a diameter of 65 mm, a height of 120 mm and a volume of 350 ml), 20 g of sodium cocoyl glutamate, 1.6 g of methyl cellulose (MC-1) as described in Synthesis Example 1, and 0.4 g of hydroxypropyl methyl cellulose (HPMC-1) as described in Synthesis Example 3 were exactly weighed, and hot water of 98° C. was added thereto to form 100.0 g of mixture. Because it was necessary to heat the mixture to a temperature of from 70° C. to 100° C. in order to dissolve the surfactant, the container was placed in a bath of 80° C., and the mixture was stirred with a stirrer at 350 to 450 rpm for 60 minutes to obtain a uniform dispersion. Then, the dispersion was stirred in a water bath of 0 to 5° C. for 40 minutes to cause dissolution, whereby obtaining a cleaning composition.

<Physical Properties of the Cleaning Composition>

The physical properties of the cleaning composition were measured as described below, and the results are shown in Table 2.

(Viscosity)

The viscosity of the cleaning composition was determined, using the cleaning composition itself as the sample for the measurement, with an Ubbelohde-type viscometer in accordance with the Viscosity Measurement by Capillary Tube Viscometer described in General Tests in the Japanese Pharmacopoeia 17th Edition.

(Zeta Potential)

The zeta potential of the cleaning composition was determined, using the cleaning composition itself as the sample for the measurement, with a zeta potential analyzer ELSZ-2000 (from Otsuka Electronics Co., Ltd.). The conditions for measurement were as follows:

Conditions for Measurement
   Temperature for measurement: 25° C.
   Instrument for measurement: Flow cell <Foam Height>

The foam height was determined with Dynamic Foam Analyzer DFA100 (product of KRUSS GmbH). The foam height is an index of foamability, and is automatically determined by Dynamic Foam Analyzer DFA100. The conditions for measurement and foam generation were as follows:

Conditions for Measurement
   Measurement tool: Glass column with a prism (inner diameter 40 mm×height 250 mm×flange 75 mm); and Filter plate (40-100 μm)
   Field of view: 9.7×6.6 μm/pixel Conditions for Foam Generation
   Cleaning composition: 50 g
   Gas flow time: 20 seconds
   Gas flow rate: 0.6 L/min
   Measurement time: 15 minutes <Foam Retention Time>

The foam retention time was determined with Dynamic Foam Analyzer DFA100 (from KRUSS GmbH). The foam retention time is an index of the foam stability, and was evaluated by detection of disappearance of foam within 15 minutes after the generation of foam with Dynamic Foam Analyzer DFA100. The conditions for measurement and foam generation were the same as those for the measurement of foam height.

<Average Bubble Diameter of Foam>

The average bubble diameter of foam was determined with Dynamic Foam. Analyzer DFA100 (KRUSS GmbH). The average bubble diameter of foam is an index of the foam fineness, and was measured as an average bubble diameter obtained at 20 seconds after the generation of foam with Dynamic Foam Analyzer DFA100. The conditions for measurement and foam generation were the same as those for the measurement of foam height.

<Foam Firmness>

The foam firmness was determined with Curdmeter MAX ME-500 (product of Asuka Kiki Company). The foam firmness is an index of the foam resilience, and was measured on the foam generated with an AWAKOBO Handy (product of The Buyer's, Inc.). The conditions for measurement were as follows.
   Measurement jig: ϕ16 mm
   Initial load of spring: 100 g
   Lifting speed of sampling stage: 0.36 cm/s
   Mass of foam: 6.5 g <Sensory Evaluation by Panelists>

Sensory evaluation was carried out by five panelists on the foamability, foam stability, foam fineness, and foam resilience. The cleaning composition was placed in an AWAKOBO Handy (product of The Buyer's, Inc.), and the foam dispensed on a hand by pumping the bottle three times was evaluated according to the following criteria.

(Evaluation Criteria)
   "A": all of the five panelists rated as good;
   "B": 3 or 4 of the five panelists rated as good;
   "C": 1 or 2 of the five panelists rated as good; and
   "D": none of the five panelists rated as good.

Examples 2-10 and Comparative Examples 1-3

In each of the Examples and Comparative Examples, a cleaning composition was produced in the same manner as in Example 1 except that a surfactant, methyl cellulose, hydroxypropyl methyl cellulose and a solvent listed in Table 2 were used. Each of the cleaning compositions was evaluated for the physical properties in the same manner as in Example 1, and the sensory evaluation was also conducted by panelists. The results are shown in Table 2. In Table 2, "MC" stands for methyl cellulose, and "HPMC" stands for hydroxypropyl methyl cellulose.

TABLE 2

| | components (% by mass) | | | | physical properties | | |
|---|---|---|---|---|---|---|---|
| | surfactant | MC | HPMC | solvent | viscosity (mPa·s) | zeta potential (mV) | foam height (mm) |
| Eample 1 | Na cocoyl glutamate (20) | MC-1 (1.6) | HPMC-1 (0.4) | purified water (78) | 40 | −35 | 165 |
| Example 2 | Na cocoyl glutamate (20) | MC-1 (1.2) | HPMC-1 (0.8) | purified water (78) | 45 | −36 | 170 |
| Example 3 | Na cocoyl glutamate (20) | MC-1 (1.0) | HPMC-1 (1.0) | purified water (78) | 48 | −33 | 195 |
| Example 4 | Na cocoyl glutamate (15) | MC-1 (1.2) | HPMC-1 (0.8) | purified water (83) | 38 | −30 | 160 |
| Example 5 | Na cocoyl glutamate (20) | MC-2 (1.2) | HPMC-1 (0.8) | purified water (78) | 44 | −38 | 180 |
| Example 6 | Na laureth sulfate (15) | MC-1 (1.2) | HPMC-1 (0.8) | purified water (83) | 46 | −49 | 195 |
| Example 7 | Na laureth sulfate (15) | MC-1 (0.8) | HPMC-1 (1.2) | purified water (83) | 50 | −48 | 200 |
| Example 8 | Na laureth sulfate (15) | MC-2 (1.0) | HPMC-1 (1.0) | purified water (83) | 45 | −50 | 200 |
| Example 9 | potassium laurate (15) | MC-1 (1.2) | HPMC-1 (0.8) | purified water (83) | 54 | −52 | 195 |
| Example10 | potassium laurate (15) | MC-2 (1.2) | HPMC-1 (0.8) | purified water (83) | 52 | −51 | 205 |
| Comp. Ex. 1 | Na cocoyl glutamate (20) | MC-1 (2.0) | — | purified water (78) | 43 | −37 | 145 |
| Comp. Ex. 2 | Na cocoyl glutamate (20) | MC-2 (2.0) | — | purified water (78) | 39 | −36 | 150 |
| Comp. Ex. 3 | Na cocoyl glutamate (20) | — | HPMC-1 (2.0) | purified water (78) | 45 | −33 | 160 |

| | physical properties | | | sensory evaluation by panelists | | | |
|---|---|---|---|---|---|---|---|
| | retention time (min) | av. bubble diameter (μm) | foam firmness (g) | foamability | foam stability | foam fineness | foam resilience |
| Eample 1 | 14.5 | 83 | 3.3 | B | A | B | A |
| Example 2 | 14.0 | 81 | 3.0 | B | A | B | A |
| Example 3 | 13.8 | 80 | 2.8 | A | B | A | B |
| Example 4 | 14.0 | 85 | 3.0 | B | A | B | A |
| Example 5 | 15.0 | 78 | 3.1 | B | A | A | A |
| Example 6 | 13.4 | 82 | 3.0 | A | B | B | A |
| Example 7 | 13.0 | 79 | 2.4 | A | B | A | B |
| Example 8 | 14.5 | 77 | 3.0 | A | A | A | A |
| Example 9 | 13.0 | 81 | 3.3 | A | B | B | A |
| Example10 | 14.6 | 76 | 3.4 | A | A | A | A |
| Comp. Ex. 1 | 12.0 | 93 | 3.2 | D | D | B | A |
| Comp. Ex. 2 | 15.0 | 85 | 3.4 | D | A | B | A |
| Comp. Ex. 3 | 10.0 | 75 | 2.2 | B | D | A | D |

From the results obtained by Dynamic Foam Analyzer DFA100, the curdmeter and the sensory evaluation by five panelists, it is evident that all of the five panelists rated the foamability as good when the foam height is 195 mm or more; 3 or 4 of the five panelists rated the foamability as good when the foam height is 160 mm or more and less than 195 mm; and none of the five panelists rated the foamability as good when the foam height is 150 mm or less.

It is also evident that all of the five panelists rated the foam stability as good when the foam retention time is 14 minutes or more; 3 or 4 of the five panelists rated the foam stability as good when the foam retention time is 13 minutes or more and less than 14 minutes; and none of the five panelists rated the foam stability as good when the foam retention time is 12 minutes or less.

It is evident that all of the five panelists rated the foam fineness as good when the average foam diameter is 80 μm or less; 3 or 4 of the five panelists rated the foam fineness as good when the average foam diameter is from 81 μm to 93 μm.

It is evident that all of the five panelists rated the foam resilience as good when the foam firmness is 3.0 g or more; 3 or 4 of the five panelists rated the foam resilience as good when the foam firmness is 2.4 g or more and less than 3.0 g; and none of the five panelists rated the foam resilience as good when the foam firmness is 2.2 g or less.

Thus, at least 3 panelists rated as good for the foamability, foam stability, foam fineness, and foam resilience in Examples 1 to 10.

Comparing the results of the physical properties and sensory evaluations by the panelists of Examples 2 and 5 with those of Examples 9 and 10, the results of Examples 5 and 10, in which MC-2 having storage modulus G'(65° C.) of 2,100 Pa, as measured at 65° C. in a 1.5% by mass aqueous solution thereof, was used as the methyl cellulose, are generally superior over those of Examples 2 and 9 in which MC-1 was used.

As demonstrated above, a cleaning composition comprising both methyl cellulose and hydroxypropyl methyl cellulose has excellent foamability, and can easily produce stable and fine foam with resilient texture.

The invention claimed is:

1. A cleaning composition comprising a surfactant, methyl cellulose, hydroxypropyl methyl cellulose, and a solvent,
    wherein a mass ratio of the methyl cellulose to the hydroxypropyl methyl cellulose is in a range of from 40:60 to 80:20.

2. The cleaning composition according to claim 1, wherein each of the methyl cellulose and the hydroxypropyl methyl cellulose has a viscosity at 20° C. of 1.0 to 100.0 mPa·s, as measured in a 2% by mass aqueous solution.

3. The cleaning composition according to claim 1, wherein the methyl cellulose has a storage modulus at 65° C.: G'(65° C.) of from 100 to 2,500 Pa, as measured in a 1.5% by mass aqueous solution.

4. The cleaning composition according to claim 1, wherein the surfactant is an anionic surfactant.

5. The cleaning composition according to claim 2, wherein the methyl cellulose has a storage modulus at 65° C.: G'(65° C.) of from 100 to 2,500 Pa, as measured in a 1.5% by mass aqueous solution.

6. The cleaning composition according to claim 2, wherein the surfactant is an anionic surfactant.

7. The cleaning composition according to claim 3, wherein the surfactant is an anionic surfactant.

8. The cleaning composition according to claim 5, wherein the surfactant is an anionic surfactant.

* * * * *